April 14, 1942. E. MAGNONE Plant Pat. 509

GRAPE

Filed July 21, 1941 2 Sheets-Sheet 1

ERNEST MAGNONE
INVENTOR,

By Francis C. Huebner
ATTORNEY.

April 14, 1942. E. MAGNONE Plant Pat. 509

GRAPE

Filed July 21, 1941 2 Sheets-Sheet 2

ERNEST MAGNONE
INVENTOR,

By Francis C. Huebner
ATTORNEY.

Patented Apr. 14, 1942

Plant Pat. 509

UNITED STATES PATENT OFFICE

509

GRAPE

Ernest Magnone, Sanger, Calif.

Application July 21, 1941, Serial No. 403,349

1 Claim. (Cl. 47—62)

My invention relates to a plant invention or discovery, and more particularly to a new variety of grapes having very few soft seeds, of medium size, having a taste resembling the taste of a muscat variety, and ripening very early in the season.

The drawings which accompany this specification illustrate in Fig. 1 a bunch of grapes of the variety claimed having a measuring stick photographed therewith to show the relative size of the berries. This figure shows the grapes when picked from the vine.

Figure 1:
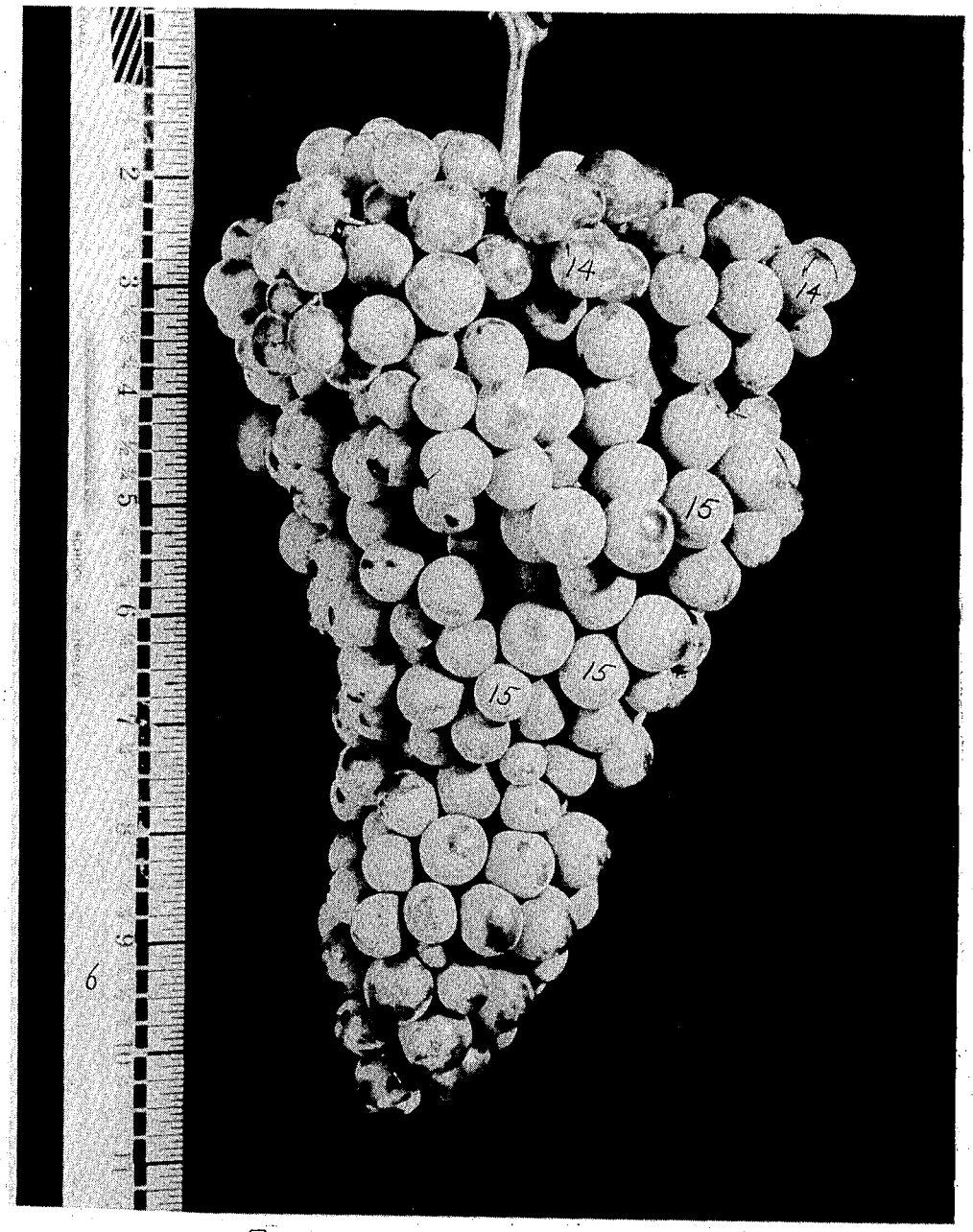

The following is a more minute description of the species: The trunk is of medium size. The bark is smooth when young, but becomes shreddy as it gets older, similar to most grapes. The bark is adherent to the trunk. Canes are medium in length, and medium in number. Canes are medium straight, and the buds are from 3 to 4 inches apart, patterning after the muscat type. The color of the buds is a reddish hue. The nodes are roundish, but are not consistent as some may be termed angular. The internodes are comparatively short, running from 3 inches to four and one-half inches. It is here noted that if the soil is not conducive to growth, and if the water supply is not ample, the internodes may be shorter than about specified, whereas in soil very highly productive with sufficient moisture the growths may be larger and longer than herein stated. These specifications relate to the grape as grown on ordinary soil with sufficient moisture.

The tendrils are intermittent but plentiful, are medium slender and mostly trifurcated at the ends, some however being bifurcated. They are generally smooth.

The flowers bloom at approximately the same period in which the Thompson Seedless raised in an adjoining patch, blooms. The flowers are fertile as indicated by a heavy crop. The stamens are upright.

In the drawings the top of the leaf is shown as 7 and the reverse, or under face of the leaf, is shown as 8. As noted in the drawings, Fig. 2, as compared with the measure 6 shown as Fig. 3, the leaves are medium small, are medium roundish and thin. The upper surface of the leaves is dark green and medium dull. The under surface is a light green. The pubescence is smooth. The leaf has five poorly defined lobes. The terminal lobe is obtuse. The petiolar sinus is deep compared with other sinuses on the leaf and sometimes overlaps when the leaf is vigorous. The basal sinus is shallow. The lateral sinus is likewise shallow. The margin of the leaf is dentate, the teeth being wide but medium as to depth.

Figures 2, 3:
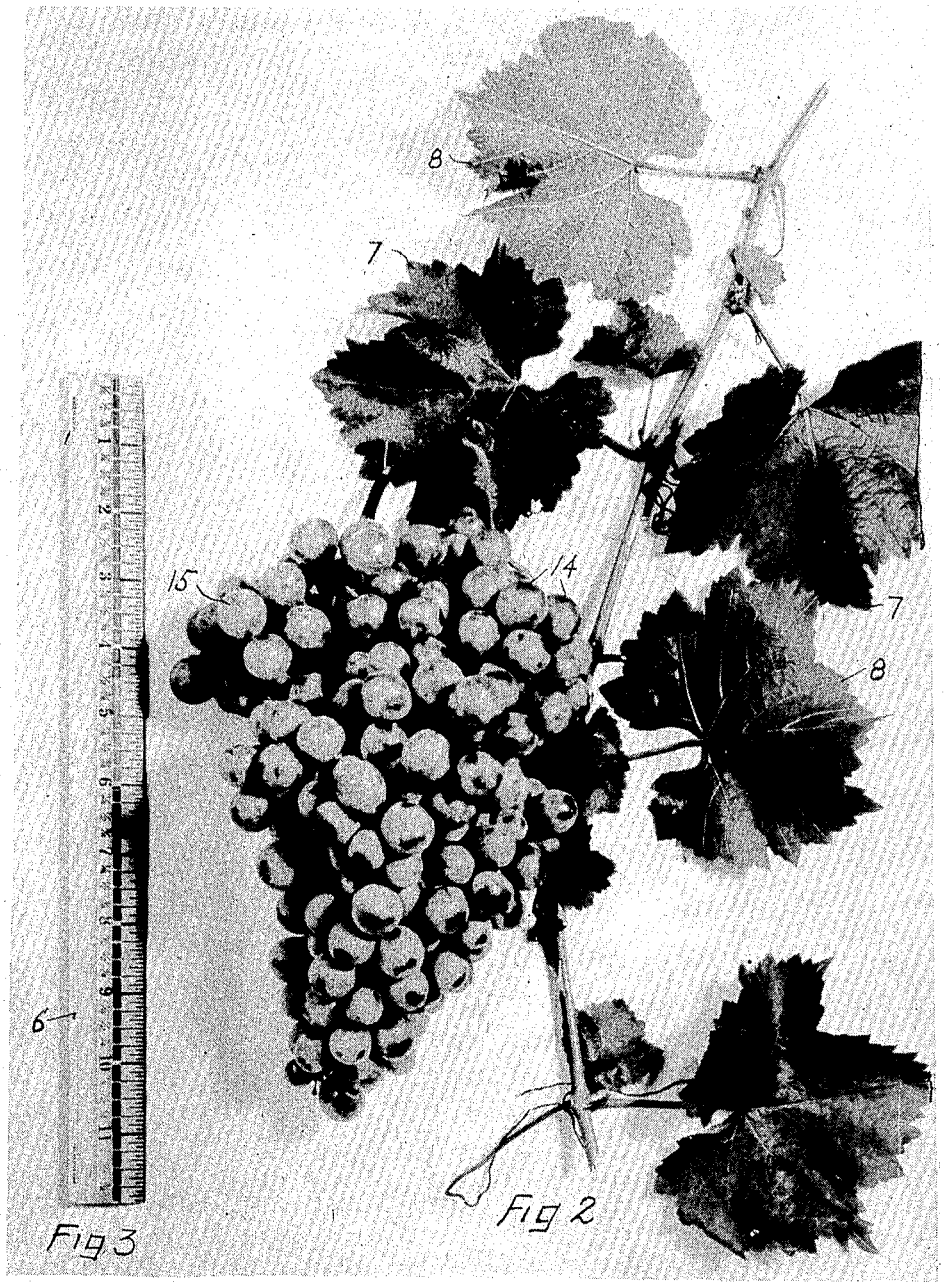
Fig. 2 shows a bunch of grapes of the variety claimed after being picked from the vine for ten days and kept in an ordinary house refrigerator, also showing the two faces of leaves, the stem, and tendrils.
Fig. 3 shows a measure for Fig. 2.

Referring to the fruit, in Fig. 1 the fruit 10 was photographed within a few hours after it was picked. It is noted that the berries designated 14 had the bloom slightly rubbed before the photograph was taken, which is not natural for the fruit. Berries designated 15 did not have the bloom disturbed. The date of ripening of the fruit runs from June 10 to July 10, depending on the character of the season, and the location. It is here noted that all of the experiments and descriptions herein set forth were located in Fresno County, California. Fig. 2 shows this variety of grapes which have been held in cold storage for approximately 10 days the time necessary for shipment from California to the eastern coast of the United States. In other experiments the fruit has been held in cold storage for 18 days without material defects, hence we allege that the shipping qualities are good.

The clusters of grapes are medium in size, are wide in width and medium in length. The bunches are approximately conical, but not consistent in carrying that shape. They are not double shouldered. The berries are medium compact on the bunch.

The peduncle is medium in length and medium in thickness. The pedicel is likewise medium in length and medium in thickness and medium in smooth outer surface.

The berry has good adherence to the stem, is medium, and uniform in size, very few shot berries, is spherical in shape, has a greenish color until ripe and then an amber color. The skin of the berry is medium thin, and adheres to the pulp. The pulp, or meat is greenish translucent in color, is tender, but firm, and is medium juicy. The pulp is clear and sweet. The quality of the berry is very good, the flavor being of the muscat type. An average bunch of the fruit was tested on July 1, 1941, and showed 17.9% sugar and 89% acidity. On July 14 an average bunch, or bunches of the fruit tested 19% sugar. It is noted that different years vary in the dates of ripening of all kinds of fruit in central California, and the year 1941 shows that the fruit is about two weeks later in ripening than in 1940

The seeds vary, the average of the large type of berries having 3 soft seeds therein, and the smaller berries running from seedless to 2 seeds.

The principal use of the fruit is for market, although raisins and wine can be made therefrom.

The origin of the variety is from muscat seed which was planted, and thereafter duly cared for, and propagated by grafting and budding.

Having described my new variety of grapes, I claim as new and ask for Letters Patent:

The new variety of grapes described, having as its main features, a berry of the muscat type of flavor, ripening very early in the season, of good keeping qualities, and prolific in bearing.

ERNEST MAGNONE.